United States Patent
Johnson et al.

(10) Patent No.: US 8,771,332 B2
(45) Date of Patent: Jul. 8, 2014

(54) MULTI-LAYER BALLOON DESIGN FOR USE IN COMBINATION WITH CATHETER ASSEMBLIES, AND METHODS OF MAKING THE SAME

(75) Inventors: Patricia Johnson, Galway (IE); Sean O'Connor, Gort (IE); Raymond Langan, Galway (IE); Michael McGuinness, Hollymount (IE); Kieran Kelly, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 415 days.

(21) Appl. No.: 12/129,210

(22) Filed: May 29, 2008

(65) Prior Publication Data

US 2009/0299450 A1  Dec. 3, 2009

(51) Int. Cl.
*A61F 2/06* (2013.01)
*A61M 25/10* (2013.01)

(52) U.S. Cl.
CPC ....... *A61M 25/10* (2013.01); *A61M 2025/1031* (2013.01); *A61M 25/1029* (2013.01)
USPC ........................................ 623/1.11; 623/1.42

(58) Field of Classification Search
USPC .................. 604/19, 48, 93.01, 96.01, 103.01; 606/191–192, 194; 623/1.11, 1.15, 623/1.42, 1.44, 1.46, 1.43
See application file for complete search history.

(56) References Cited

U.S. PATENT DOCUMENTS

| | | | |
|---|---|---|---|
| 4,417,576 A * | 11/1983 | Baran | 128/207.15 |
| 5,509,899 A | 4/1996 | Fan et al. | |
| 5,653,689 A * | 8/1997 | Buelna et al. | 604/103.09 |
| 6,545,097 B2 | 4/2003 | Pinchuk et al. | |
| 6,790,228 B2 | 9/2004 | Hossainy et al. | |
| 6,855,770 B2 | 2/2005 | Pinchuk et al. | |
| 6,899,731 B2 | 5/2005 | Li et al. | |
| 7,014,654 B2 | 3/2006 | Welsh et al. | |
| 7,105,175 B2 | 9/2006 | Schwarz | |
| 2003/0195456 A1 * | 10/2003 | Robertson | 604/8 |
| 2004/0191443 A1 | 9/2004 | Hamlin | |
| 2004/0215169 A1 | 10/2004 | Li | |
| 2006/0129727 A1 | 6/2006 | Park | |
| 2006/0212106 A1 | 9/2006 | Weber et al. | |
| 2007/0299392 A1 * | 12/2007 | Beyar et al. | 604/96.01 |

FOREIGN PATENT DOCUMENTS

| | | |
|---|---|---|
| EP | 0768097 | 4/1997 |
| JP | 06063145 | 3/1994 |

* cited by examiner

*Primary Examiner* — Ashley Fishback
(74) *Attorney, Agent, or Firm* — Vidas, Arrett & Steinkraus

(57) ABSTRACT

An expandable medical device having a static state and at least one expanded state, the expandable medical device in the static state including at least one first inner layer and at least one second outer layer, the outer layer having an inner surface and an outer surface, the outer layer having a closed lattice in the inner surface or the outer surface of the outer layer, wherein the lattice is open when the expandable medical device is in the at least one expanded state, and methods of making the same.

13 Claims, 6 Drawing Sheets

MULTI-LAYER BALLOON DESIGN FOR USE IN COMBINATION WITH CATHETER ASSEMBLIES, AND METHODS OF MAKING THE SAME

FIELD OF THE INVENTION

The present invention relates to the field of insertable and implantable medical devices, in particular, to catheter delivery systems for use therewith.

BACKGROUND OF THE INVENTION

Atherosclerotic cardiovascular disease is common, and is caused by a narrowing of the arterial lining due to atherosclerotic plaques. When plaque builds up, this is referred to in the art as stenosis. One method commonly employed to relieve arterial stenosis resulting from plaque build-up is percutaneous transluminal coronary angioplasty, or balloon angioplasty. PTCA or balloon angioplasty, is a non-invasive, non-surgical means of treating coronary arteries.

This technique consists of inserting a non-inflated balloon catheter into the affected artery. Dilation of the diseased segment of artery is accomplished by inflating the balloon which pushes the atherosclerotic lesion outward, compressing the stenosis and enlarging the arterial diameter.

To help prevent arterial closure, repair dissection, or prevent restenosis, a physician can also implant an intravascular prosthesis, or a stent, for maintaining vascular patency inside an artery or other vessel at the lesion.

Stents are also used for a variety of other purposes including maintaining the patency of any physiological conduit including arteries, veins, vessels, the biliary tree, the urinary tract, the alimentary tract, the tracheobronchial tree, the genitourinary system, and the cerebral aqueduct.

In combination with a stent, it has further been found to be advantageous to employ pharmacologically active therapeutic agents, such as those in the form of a drug eluting coating, to reduce the amount of restenosis caused by intimal hyperplasia.

Stents may be may either be self-expanding or balloon expandable. For the latter type, the stent is often delivered on a balloon and the balloon is used to expand the stent.

Whether the balloon is used for POBA or for stent delivery, one consideration is withdrawal resistance of the balloon after use. Depending on the material used to manufacture the balloon and the stent, and possibly stent coating, there may be friction between the balloon and stent surfaces. Also, if a sufficient amount of time is not allowed for the balloon to fully deflate after use, there may be resistance upon attempts to withdraw the balloon from the treatment site.

One way to remedy this is to provide a lubricious coating between the outer balloon surface and the inner stent surface.

Other considerations in the manufacture of a balloon include reliable inflation to a predetermined diameter when the balloon is infused with inflation media, and the balloon must have the ability to collapse and fold to a minimal, radially compact cross-sectional shape after use to facilitate withdrawal.

It can be difficult to achieve all of these properties when constructing a balloon from a single polymer material.

There remains a need for innovative and improved balloon construction to achieve the desired balance of properties.

SUMMARY OF THE INVENTION

In one aspect, the present invention relates to an expandable medical device having at least one inner layer and at least one outer layer with a lattice formed in the inner surface or the outer surface of the outer layer, the device having at least one static state, at least one expanded state and at least one deflated state, in the expanded state the lattice is open, and in the static state the lattice is closed.

Suitably, both the inner and outer layer are polymeric.

In various embodiments, the intermediate layer may include a variety of coatings. In specific embodiment, the intermediate layer includes at least one lubricious polymer material, at least one therapeutic agent(s), or a combination thereof.

The expandable medical device may be employed in combination with a catheter assembly. Optionally, the expandable medical device may be employed in combination with a stent.

In another aspect, the present invention relates to a variety of methods of making the expandable medical device including the steps of forming an inner and an outer layer, and forming a lattice in the inner surface or the outer surface of the outer layer. The inner and outer layer can be formed simultaneously, or first individually formed prior to assembly.

The intermediate layer can be formed simultaneously with the inner and outer layer, or, the intermediate layer can be injected between the inner and outer layer as a liquid mixture, after the inner and outer layer have been assembled.

The lattice can be formed in the inner surface or the outer surface of the outer layer prior to assembly, or can be formed in the outer surface after forming or assembly of the inner and outer layer.

These and other aspects, embodiments and advantages of the present invention will become immediately apparent to those of ordinary skill in the art upon review of the Detailed Description and Claims to follow.

BRIEF DESCRIPTION OF THE DRAWINGS

FIGS. 8A-10A are radial cross-sections taken at 8A-8A, 9A-9A and 10A-10A in FIGS. 8, 9 and 10 respectively.

DETAILED DESCRIPTION OF THE PREFERRED EMBODIMENTS

Figure 1:
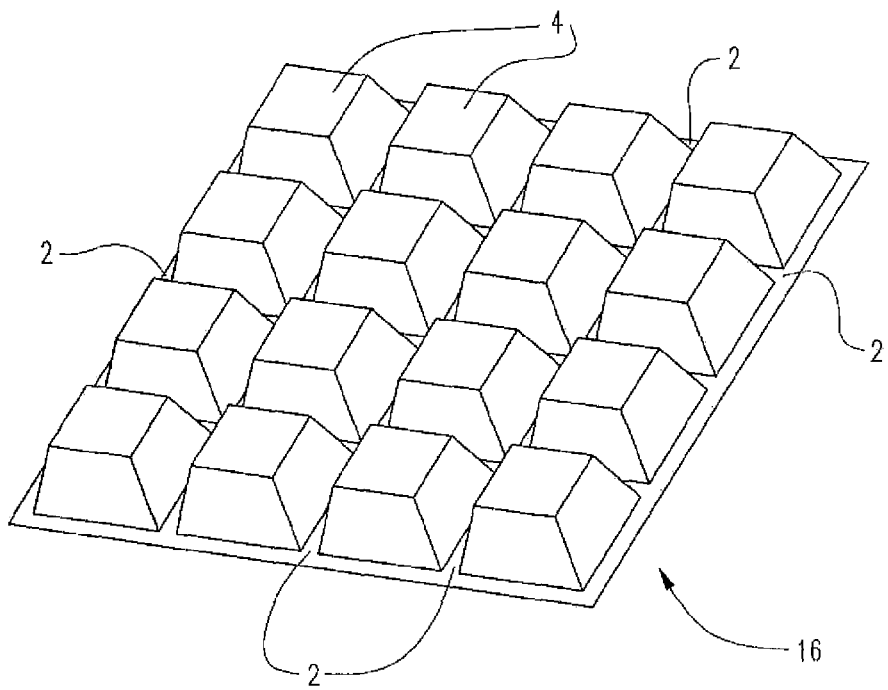
FIG. 1 is a flat perspective view of one embodiment of a lattice formed in the outer layer of a multilayer medical device according to the invention.

While this invention may be embodied in many different forms, there are described in detail herein specific preferred embodiments of the invention. This description is an exemplification of the principles of the invention and is not intended to limit the invention to the particular embodiments illustrated.

All US patents and applications and all other published documents mentioned anywhere in this application are incorporated herein by reference in their entirety.

In one aspect, the present invention is directed to a multi-layer expandable medical device having at least one static state, at least one expanded state, and at least one deflated state. The outer layer of the multilayer expandable medical device, in the at least one static state, has a closed structure, and in the at least one expanded state, the outer layer has a lattice-like open structure. This allows an intermediate layer to be exposed when the medical device is in its at least one expanded state.

As used herein, the static state shall refer to the balloon as formed, prior to expansion or deflation.

Suitably, the intermediate layer is a lubricious coating layer, a drug-eluting layer, or a combination thereof.

The expandable medical device herein may find particular utility for delivery of medical devices such implantable medical prosthesis such as stents and stent grafts wherein the intermediate layer is a lubricious coating layer. In such an embodiment, during delivery and prior to deployment of the implantable medical prosthesis, the outer layer has a closed structure and the intermediate lubricious layer is unexposed. During deployment, wherein the expandable medical device is expanded to its at least one expanded state, the outer layer is in its open lattice-like structure, exposing the lubricious layer which in turn can facilitate withdrawal of the expandable medical device once the implantable prosthesis has been deployed.

The intermediate layer may include any suitable lubricious material including both hydrophobic and hydrophilic materials, with hydrophilic materials being preferred. One example of a hydrophobic material is silicone.

Hydrophilic polymer materials may also be employed. As used herein, the term "hydrophilic" is used to refer to water having various degrees or water sensitivity including those materials that are water soluble, dispersible, dissolvable, etc. As used herein, the term "water soluble" shall include those materials which have partial solubility in water.

Suitable hydrophilic polymers include those that have non-crosslinked structures having hydrophilic groups thereon, such as —OH, —COOH, —CONH, —COO—, etc. The hydrophilicity of the polymer can be controlled by the number of such groups, as well as the polymer structure.

Examples of hydrophilic materials include, but are not limited to polyalkylene glycols such as polyethylene glycol (PEG), and modified polyalkylene glycols such as polyethylene and polypropylene oxide and hydrophilic block copolymers thereof, poly(N)-vinyl lactams, such as polyvinylpyrrolidone (PVP), polyacrylamides, cellulosics such as methyl cellulose, carboxymethyl cellulose, hydroxyethyl cellulose and hydroxypropyl cellulose, carbohydrates, sugar alcohols such as mannitol, polyols, monosaccharides, oligosaccharides, polysaccharides and modified polysaccharides such as heparin (mucopolysaccharide), polyacrylic acids such as acrylic and methacrylic acids and salts thereof with alkali metal salts with sodium and potassium salts being most common and alkaline earth metal salts, hydroxyl methacrylate (HEMA), polyvinyl alcohols, polyvinyl acetates, polyvinyl ethers, hydrophilic polyurethanes such as polyether aliphatic polyurethanes, hydrophilic polyamides, methyl vinyl ether-maleic anhydride copolymers, etc. and mixtures thereof. Copolymers formed with the same hydrophilic monomers may also be employed, for example, acrylamide and vinylpyrrolidone.

For hydrophilic polymer materials, see for example, U.S. Pat. No. 5,509,899 and U.S. Patent Publication No. 2006/0212106, each of which is incorporated by reference herein in its entirety.

Bioerodible hydrogels are suitable and in some embodiments, preferred. Examples include, but are not limited to, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other suitable hydrogels include, but are not limited to, polyvinylpyrrolidone, polyethylene oxide (polyethylene glycol), polyvinyl alcohol, etc.

The above materials are intended for illustrative purposes only and not as a limitation on the scope of the present invention.

The addition of a the lubricious coating layer can reduce the withdrawal resistance that may occur when the physician attempts to withdraw a balloon from an expanded stent without allowing sufficient time for the balloon to deflate fully. There may be friction between the material employed for forming the balloon and a stent coating, for example. The addition of a lubricious coating between the stent and balloon during deployment can aid the withdrawal of the balloon from the stent. During delivery, however, while the stent is in the crimped state on the balloon, and the balloon deflated from its static state by application of negative pressure, and then wrapped prior to crimping the stent thereon, the lubricious coating remains unexposed beneath the closed lattice of the balloon outer layer. The lubricious coating only becomes exposed upon expansion of the balloon, and breakage of the closed lattice.

The expandable medical device described herein may find particular utility as a drug delivery device for the controlled delivery of a therapeutic substance(s) wherein the intermediate layer is a drug-eluting layer. The therapeutic substance(s) begin to elute following inflation of the medical device and breakage of the closed lattice.

If it is desirable that the intermediate layer be a drug-eluting layer, any suitable therapeutic agent may be employed therein. As used herein, the terms, "therapeutic agent", "drug", "pharmaceutically active agent", "pharmaceutically active material", "beneficial agent", "bioactive agent", and other related terms may be used interchangeably herein and include genetic therapeutic agents, non-genetic therapeutic agents and cells. A drug may be used singly or in combination with other drugs. Drugs include genetic materials, non-genetic materials, and cells including those of human origin, animal origin, and those that are genetically engineered.

Examples of non-genetic materials include, but are not limited to, anti-thrombogenic agents, anti-proliferative agents, anti-inflammatory agents, analgesics, antineoplastic/antiproliferative/anti-miotic agents, anesthetic agents, anticoagulants, vascular cell growth promoters, vascular cell growth inhibitors, cholesterol-lowering agents; vasodilating agents; and agents which interfere with endogenous vascoactive mechanisms.

Examples of genetic materials include, but are not limited to, anti-sense DNA and RNA and coding DNA, for example.

Some specific examples of therapeutic agents include, but are not limited to, anti-restenosis drugs, such as paclitaxel, sirolimus, everolimus, tacrolimus, dexamethoasone, estradiol, ABT-578 (Abbott Laboratories), trapidil, liprostin, Actinomycin D, Resten-NG, Ap-17, clopidogrel and Ridogrel.

Examples of suitable drugs can be found in commonly assigned U.S. Pat. Nos. 7,105,175, 7,014,654, 6,899,731, 6,855,770 and 6,545,097, each of which is incorporated by reference herein in its entirety, and in commonly assigned U.S. Patent Application Publication No. 2004/0215169 and 2006/0129727, each of which is incorporated by reference herein in its entirety.

The drug may be provided in a liquid carrier between the at least one outer layer and the at least one inner layer, or may be provided in a polymer carrier.

Suitable polymer carriers may include biodegradable/bioresorbable polymer materials. Examples include, but are not limited to, polyhydroxyalkanoates such as poly(hydroxybutyrate) (PHB), poly(hydroxyvalerate) (PHV) and poly(hydroxybutyrate-co-valerate), polylactones such as polycapolactone (PCL), poly(L-lactic acid) (PLA), poly(glycolic acid) (PGA), poly(D,L-lactic acid), poly(lactide-co-glycolide) (PLGA), polydioxanone, polyorthoesters, polyanhydrides, poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen, hyaluronic acid, etc., and mixtures thereof. Bioabsorable polymers are disclosed in U.S. Pat. No. 6,790,228, the entire content of which is incorporated by reference herein.

Other polymer materials include block copolymers of styrene and isoprene (SIS), butadiene (SBS), ethylene/butylene (SEBS), isobutylene (SIBS), ethylene/propylene (SEPS), etc. Diblock copolymers may also find utility herein.

Other block copolymers which may be employed include polyamide-block-ether copolymers such as those available under the tradename of PEBAX® available from Arkema in Philadelphia, Pa., and polyester and copolyester elastomers such as poly(ester-block-ether) elastomers available under the tradename of HYTREL® from DuPont de Nemours & Co. and poly(ester-block-ester)

Other suitable polymer carrier materials include, polyolefins, such as ethylene and propylene homopolymers, as well as any copolymers or terpolymers of ethylene and propylene such as ethylene-vinyl acetate copolymers, ethylene (meth) acrylate copolymers, ethylene n-butyl acrylate copolymers, and grafted polyolefins such as maleic anhydride grafted polyethylene or polypropylene, and so forth.

Other suitable polymer carrier materials include, but are not limited to, polyesters, polyamides including nylon 6,6 and nylon 12, polyurethanes, polyethers, polyimides, polycarboxylic acids including polyacrylic acids, (meth)acrylates, cellulosics, polycaprolactams, polyacrylamides, polycarbonates, polyacrylonitriles, polyvinylpyrrolidones, copolymers and terpolymers thereof, etc.

The above lists are intended for illustrative purposes only, and not as a limitation on the scope of the present invention.

Of course, the therapeutic agent may be mixed with a lubricious material, for example, a hydrogel material, thereby providing an intermediate layer which has both lubriciousness, as well as drug-eluting characteristics.

As used herein, lattice shall be used to describe the pattern formed in the outer layer of the multilayer balloon structure through any suitable means such as cutting, scarring, etching, searing, embossing, etc. that weakens the layer. However, the pattern is not formed all the way through the layer. When the expandable medical balloon is in its at least one expanded state, the lattice opens at the weakened regions to expose the underlayer.

For purposes of illustration, referring now to the drawings, FIG. 1 is a partial perspective view of an outer balloon surface illustrating one embodiment of a lattice formed in the surface. Channels 2 have been formed using any suitable means such as cutting, embossing, searing, etching either chemically or mechanically, scarring, etc. These channels 2 have a thinner wall than corresponding areas 4 and are weakened as a result.

Figure 2A:
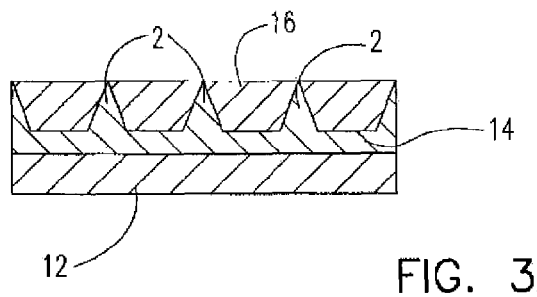
FIG. 2A is a partial radial cross-section illustrating a tri-layer configuration of an expandable medical device in a static state wherein the lattice is closed.

FIG. 2A is a partial radial cross-section of an expandable medical device having a tri-layer structure. In this embodiment, an inner layer 12, defines the expandable medical balloon. Outer layer 16 has a lattice structure with channels 2 formed into the inner surface of the outer layer. In FIG. 2A, the expandable medical device is in a static state.

Figure 2B:
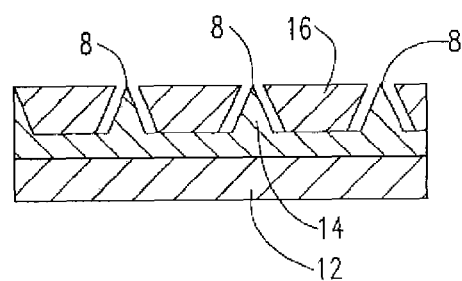
FIG. 2B is a partial radial cross-section illustrating a tri-layer configuration of an expandable medical device similar to that shown in FIG. 2A in an expanded state wherein the lattice is open.

FIG. 2B is a partial radial cross-section of an expandable medical device similar to that shown in FIG. 2A, wherein the device is in an expanded state, and the lattice in the outer layer 16, has opened. Openings 8 in the lattice structure expose the inner layer 14 which may be a lubricious layer, a drug eluting layer, or combination thereof as discussed above.

Figure 3A:
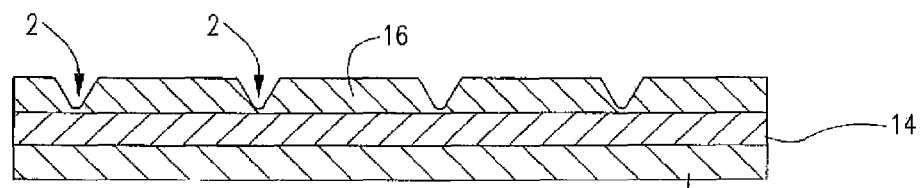
FIG. 3A is a partial radial cross-section illustrating an alternative tri-layer configuration of an expandable medical device in a static state wherein the lattice is closed similar to that shown in FIG. 1.

FIG. 3A is a partial radial cross-section of an expandable medical device having a tri-layer structure wherein the outer layer 16 has an alternative lattice structure more similar to that shown in FIG. 1 wherein channels 2 are formed in the outer surface of the outer layer as opposed to that shown in FIG. 2A. In this embodiment, an inner layer 12 defines the expandable medical balloon. In FIG. 2A, the expandable medical device is in a static state.

Figure 3B:
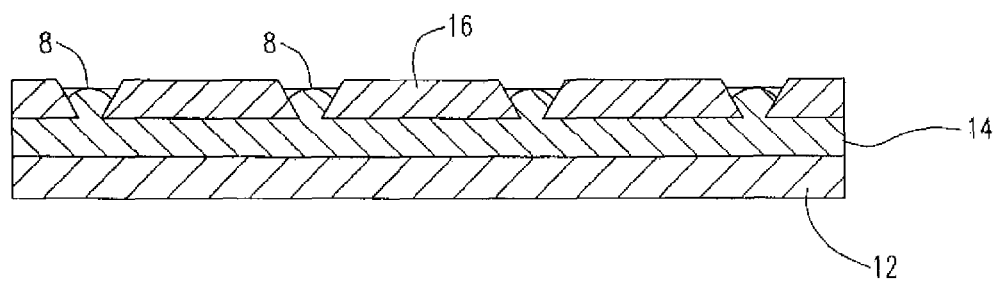
FIG. 3B is a partial radial cross-section illustrating a tri-layer configuration of an expandable medical device similar to that shown in FIG. 3A in an expanded state wherein the lattice is open.

FIG. 3B is a partial radial cross-section of an expandable medical device similar to that shown in FIG. 3A, wherein the device is in an expanded state, and the lattice in the outer layer 16, has opened. As in FIG. 2B, openings 8 in the lattice structure expose the inner layer 14 which may be a lubricious layer, a drug eluting layer, or combination thereof as discussed above.

Outer layer 16 may be formed from any polymer material and is suitably, a material that has less elasticity or expansitivity, for example, than that of the inner layer 12. Suitable outer layer materials include, but are not limited to, polyalkylene terephthalates such as polyethylene terephthalate and polybutylene terephthalate, polyethylene, polypropylene, polyamides, polycarbonate, poly(ether-block-amide) such as PEBAX® 72D available from Arkema, North America, located in Philadelphia, Pa. Of course, these polymers are intended for illustrative purposes only, and other polymers not listed herein may be employed as well.

Suitably, the inner layer 12 has superior mechanical properties to that of the outer layer 16, such as more elasticity and expansivity. Suitable materials for the inner layer 12 include, for example, any block copolymer that is more elastomeric or elastic than that of the outer layer 16. For example, if PEBAX® 72D is selected for the outer layer 16, the inner layer 12 may be formed from a more elastic PEBAX® material, for example, PEBAX® 62D, also available from Arkema. Of course, block copolymer materials need not be employed for the inner layer 12, provided that it has more elasticity than that of the outer layer 16.

The outer layer 16 may be formed from any suitable material that protects the intermediate layer and allows/controls when the intermediate layer is released. Other examples include, but are not limited to, block copolymers such as styrenic block copolymers having styrene endblocks and midblocks of butadiene, isoprene, ethylene/butylene, ethylene/propylene, etc., copolyesters, polyester-polyether block copolymers such as those available under the tradename of Hytrel®, polyurethanes, etc.

The inner layer 12 may be formed from any material suitable for POBA (plain old balloon angioplasty). Examples include, but are not limited to, thermoplastic ionomers such as those available under the tradename of Surlyn® (also referred to as polyolefin copolymers), polyesters such as polyethylene terephthalate and polybutylene terephthalate, polyamides including nylon 6,6, nylon 12 and nylon 6, polyurethanes, copolyesters, polyester-polyethers such as those available under the tradename of Arnitel® or Hytrel®, polyether-block-amides available under the tradename of Pebax®, polyolefins including polyethylene and polypropylene and copolymers and terpolymers thereof such as ethylene vinyl acetate, etc.

Again, for the above embodiment, the inner layer is selected so as to exhibit more elasticity than the outer layer.

Combinations of materials from the same family can be employed, providing that the material selected for each layer exhibit different properties. For example, a Pebax® resin that is more rigid can be employed for the outer layer, and a Pebax® resin that is more elastic for the inner layer, for example, Pebax® 7233 exhibits a higher flexural modulus than does Pebax® 7033 or Pebax® 6333.

Alternatively, the outer layer 16 may be highly elastic and the inner layer 12 is less elastic. In the case where a highly elastic material is employed for the outer layer 16, the material selected may be microporous/nanoporous material wherein the pores open when the balloon is inflated. The elasticity of the outer layer could also assist the balloon to re-wrap upon deflation allowing easier withdrawal.

Thus, the outer layer may be either rigid or elastic providing that it protects the intermediate layer and controls/allows when the intermediate layer is released.

Microfluidic channels also could be employed wherein movement of the intermediate layer is allowed with pressure driven flow upon balloon inflation or osmotic material that allows movement of the coating in one direction only upon balloon inflation could also be employed for use in forming the outer layer.

Figure 4:
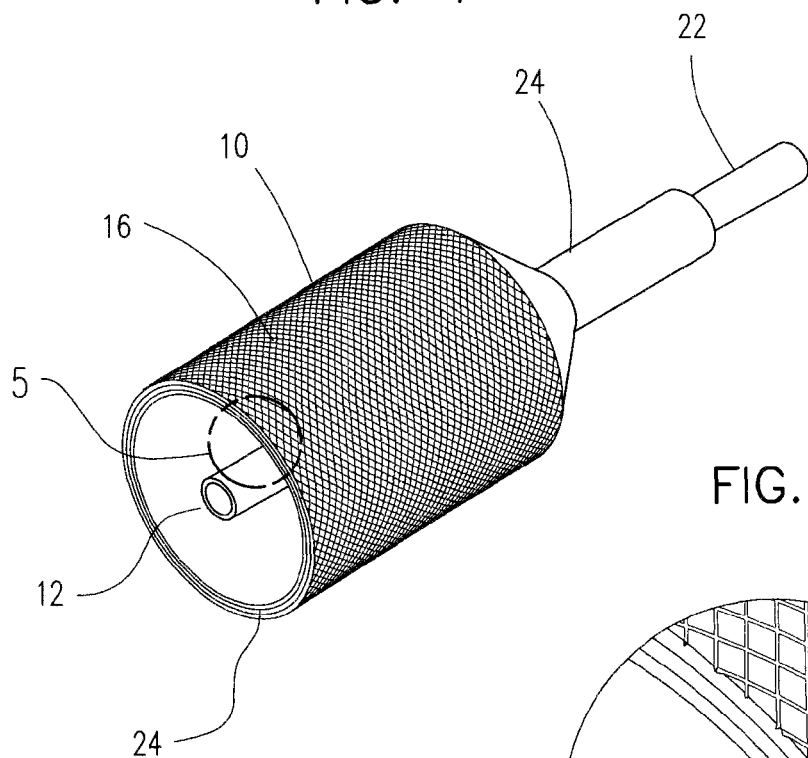
FIG. 4 is a partial perspective view of a tri-layer medical balloon disposed on a dual-layer shaft catheter assembly.

FIG. 4 illustrates a partial perspective view of a medical balloon disposed about a dual-shaft catheter assembly having an inner shaft 22 and an outer shaft 24. Balloon 10 has a tri-layer design including an outer layer 16 having a diamond lattice formed therein, an intermediate layer 14, and an inner layer 12 which defines the expandable medical balloon structure.

As discussed above, intermediate layer 14 can be lubricious, drug-eluting, or a combination thereof. Of course, other types of coatings can be employed as well depending on the end result desired. For stent delivery, it may be desirable to have a lubricious coating forming the intermediate layer 14. When the balloon is expanded, and the diamond lattice structure of the outer layer 16 opens, the lubricious coating is exposed. Lubricious coatings on the outer surface of a balloon may have an adverse impact on stent delivery due to slippage of the stent on the balloon. However, lubricious coatings decrease withdrawal resistance of the balloon once the stent has been deployed. Therefore, exposing the lubricious coating only during deployment of the stent, provides a desirable combination of properties to the balloon.

Again, FIGS. 2 and 3 may be referred back to for illustration on opening of the lattice once the expandable medical balloon has been expanded.

Figure 5:
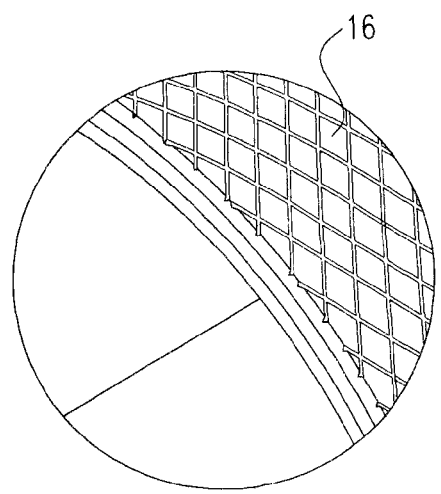
FIG. 5 is an exploded view taken at section 5 in FIG. 4 illustrating the a lattice formed in the outer layer.
Figure 6:
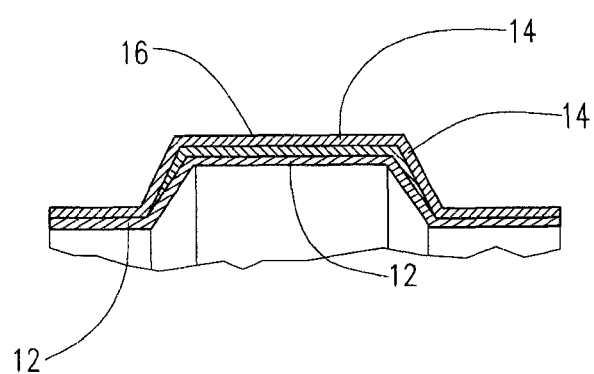
FIG. 6 is a partial longitudinal cross-section showing a tri-layer balloon.

FIG. 5 is a partial exploded view of the tri-layer balloon structure taken at section 5 in FIG. 4. FIG. 6 is a partial longitudinal cross-section of a balloon as shown in FIGS. 4 and 5.

FIGS. 7-10A illustrate various embodiments of a balloon according to the present invention and include a variety of lattices (patterns) which may be formed into the outer balloon layer.

Figure 7:
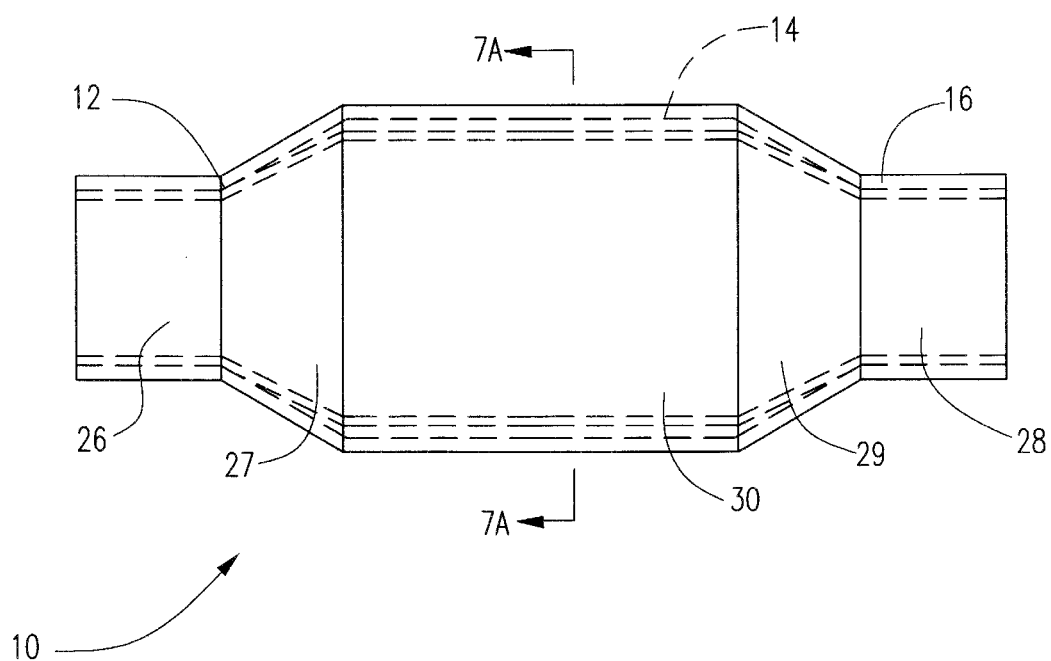
FIG. 7 is a longitudinal cross-section of an expandable medical balloon having a tri-layer structure wherein the outer layer is a generic representation of the lattice in the outer layer.
Figure 7A:
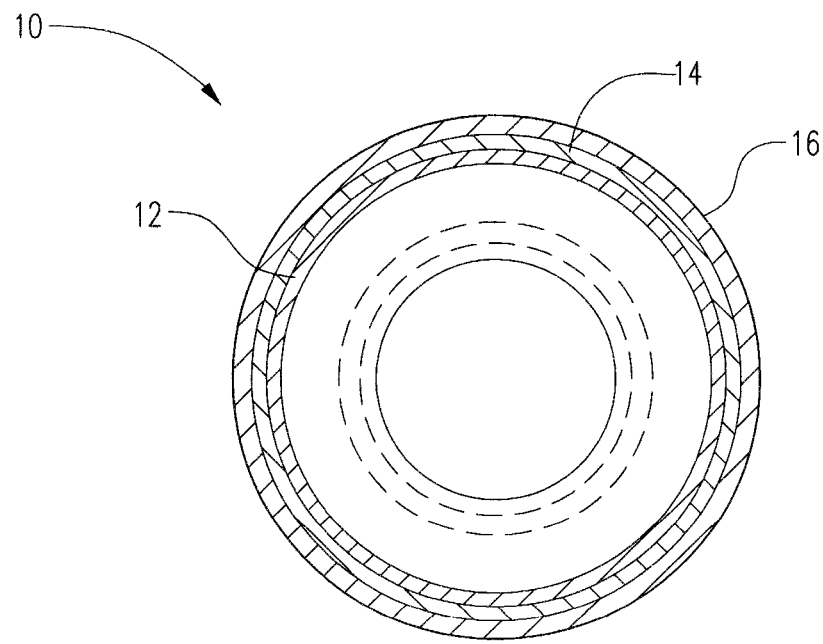
FIG. 7A is a radial cross-section taken at section 7A-7A in FIG. 7.

FIG. 7 is a longitudinal cross-section of a balloon 10 having a tri-layer structure. The outer layer 16 which includes the lattice, is shown generically in this figure, as the lattice could be formed of an endless array of patterns. Balloon 10 is shown with an intermediate layer 14 and an inner layer 12. Balloon 10 has waist portions 26, 28, cone portions 27, 29 and a body portion 30. The outer layer 16 may be formed on any portion or combination of these portions. For example, it may be desirable to form the outer layer 16 on only the body portion 30. FIG. 7A is a radial cross-section taken at section 7A-7A in FIG. 7.

Figure 8:
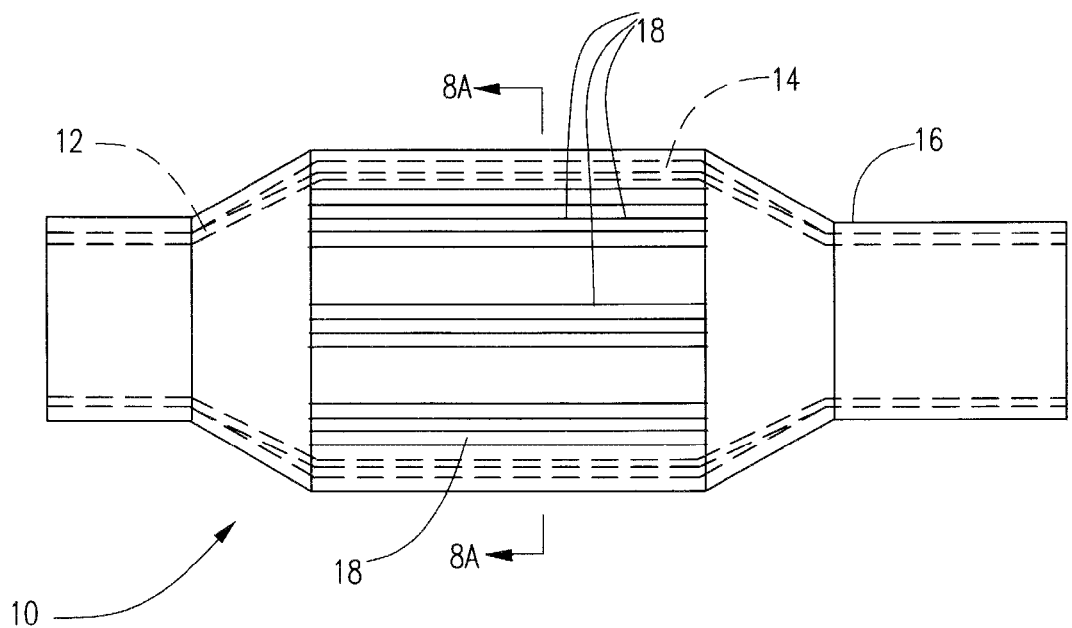
FIGS. 8-10 are longitudinal cross-sections illustrating various embodiments of a tri-layer balloon having different lattices formed into the outer layer.
Figure 8A:
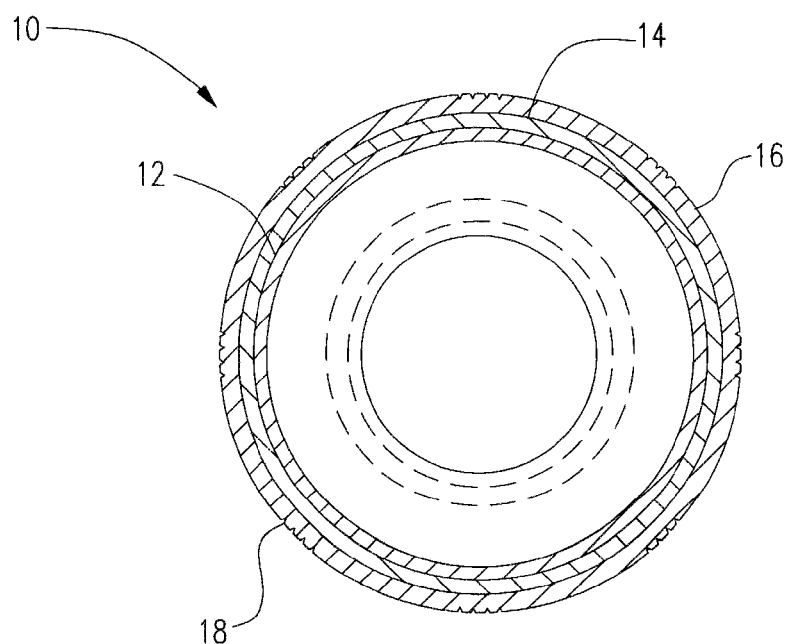

FIG. 8 is a longitudinal cross-section illustrating one embodiment of a balloon having a lattice formed of longitudinal channels 18 in the balloon body 30 only. FIG. 8A is a radial cross-section taken at section 8A-8A in FIG. 8.

Figure 9:
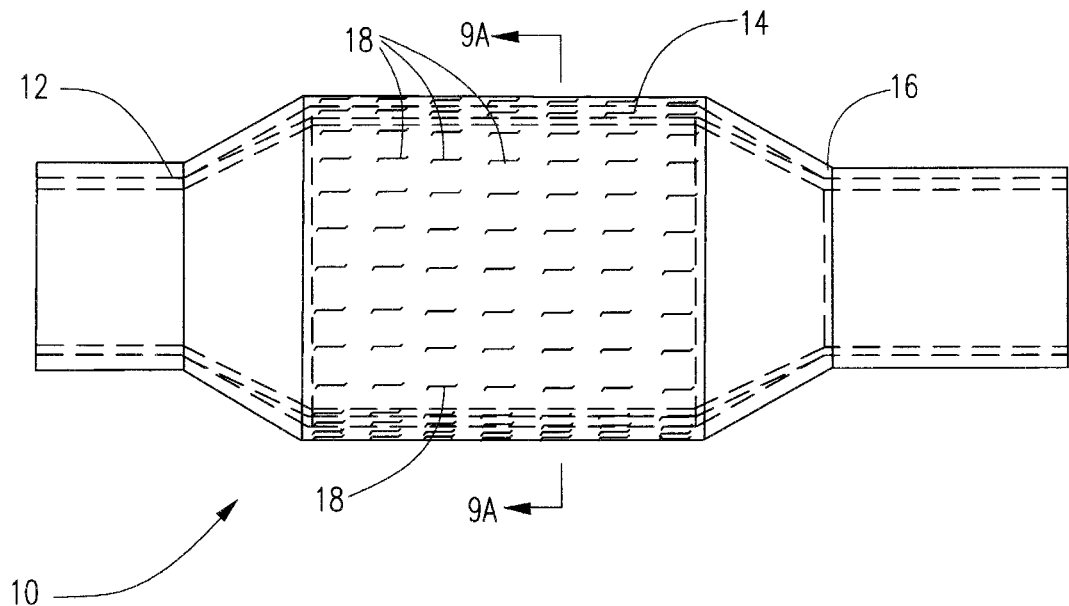
Figure 9A:
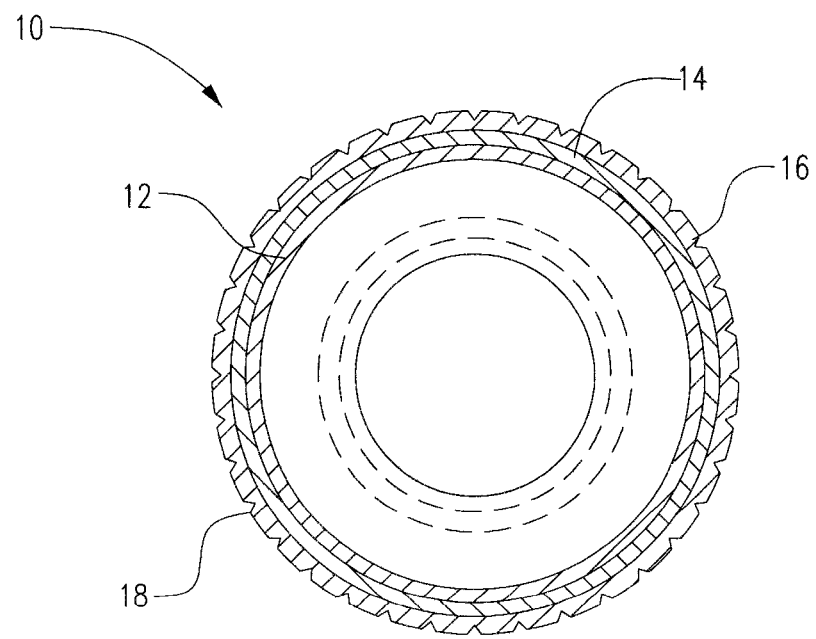

FIG. 9 is longitudinal cross-section of illustrating another embodiment of a balloon having a different lattice formed into balloon body 30. This lattice includes a plurality of channels 18 that are discontinuous on the balloon body 30. FIG. 9A is a radial cross-section taken at section 9A-9A in FIG. 9.

Figure 10:
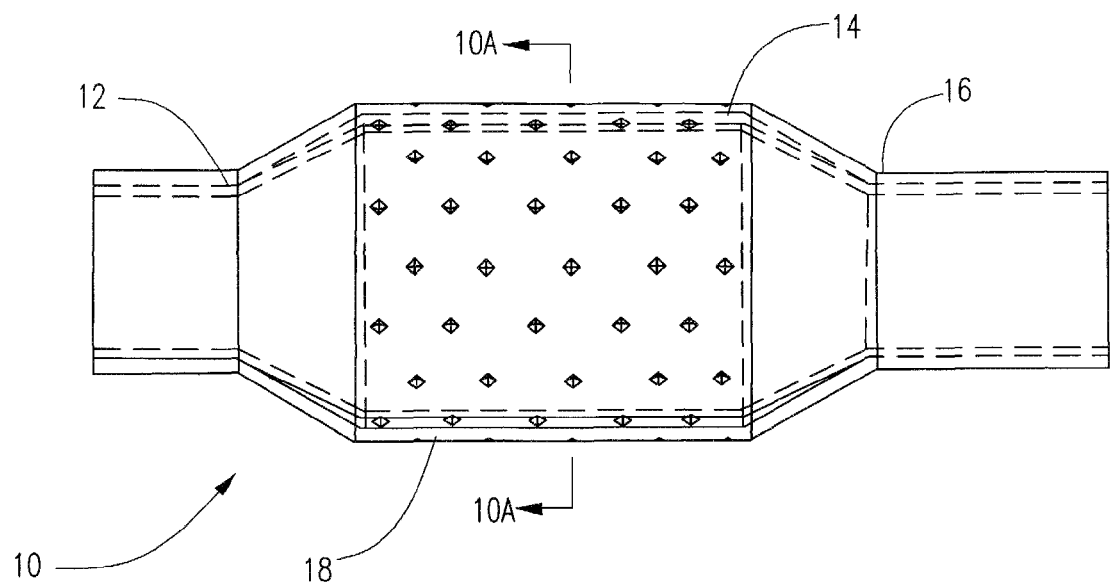
Figure 10A:
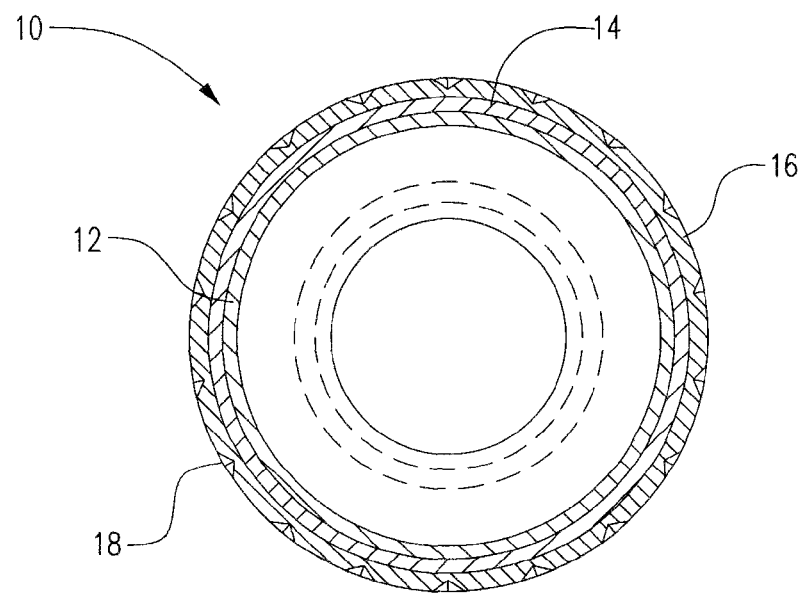

FIG. 10 is longitudinal cross-section of illustrating another embodiment of a balloon having a different lattice formed into balloon body 30. This lattice includes a plurality of marks 18 in the form of crosses 18 formed into the surface of the outer layer 16 on the balloon body 30. FIG. 10A is a radial cross-section taken at section 10A-10A in FIG. 10.

As mentioned above, there is no limit as to the lattice pattern that may be selected, and the invention is not limited as such. The lattice may be a defined repeatable pattern or may be non-regular and random.

The balloons may be formed using any suitable balloon forming process. For example, the inner layer, defining the balloon structure, may be extruded as a tubular balloon preform. The intermediate layer can be applied in a variety of ways including co-extrusion with the inner layer, by spraying, dipping, brushing, etc. The intermediate layer can be applied to the whole balloon structure, or to any portion thereof as desired.

In some performing processes, the tubular member is stretched, and the ends then dipped in glycerin leaving the ends crystallized and leaving a predetermined length of the central portion of the tubular preform balloon uncrystallized.

The preform is then inserted into a balloon forming mold and radially expanded using nitrogen, for example.

One method of adding the outer layer having the lattice is to first radially expand this outer layer in a mold that has blades inside the mold, the blades cutting the lattice pattern in the outer surface of the outer layer as desired. Alternatively, this layer can be formed in a standard balloon mold, no blades, and then the lattice can be cut, etched, embossed, seared, etc. on the inner surface of the outer layer. The inner layer with the intermediate layer, suitably an intermediate layer with some adhesive characteristics, can be radially expanded in the same mold. Heat treating can then facilitate adhesively bonding the inner layer to the outer layer via the intermediate layer.

Alternatively, the balloon can be formed with the inner and outer layer only, and the intermediate layer injected between the inner and outer layer. This process may be more readily employed wherein the lattice pattern is formed on the inner surface of the outer layer. See FIGS. 2 and 3, for example, wherein there are more spaces via channels 2, that exist between the inner layer 12 and outer layer 16.

The coating can then be cured such as by drying if the coating is applied from a solvent.

Balloon folds can then be formed in the balloon, the balloon deflated and a stent crimped thereon if the balloon is employed for stent delivery.

Of course, all three layers can be simultaneously coextruded as well wherein the three different materials are combined using three different extruders. Tooling can be made to the correct dimension you require for your product. Intermittent coextrusion or via use of a quick shut-off valve at the crosshead can be employed to provide the outer layer on only those portions of the balloon, such as the balloon body, as desired. The lattice can be formed in the outer surface of the outer layer such as through etching, cutting, ablating, via a laser, embossing, searing, etc The coating can alternatively be injected between a coextruded inner and outer layer as well through interstices, which is more readily employed wherein the lattice is formed in the inner surface of the outer layer.

The inner layer may optionally include an adhesive for securement to the outer layer. The adhesive may be coextruded as well.

The present invention allows for the localized controlled delivery of a variety of substances to a specific target site within a patient such as during POBA (plain old balloon angioplasty) and stent delivery.

The above examples and disclosure are intended to be illustrative and not exhaustive. These examples and description will suggest many variations and alternatives to one of ordinary skill in this art. All these alternative and variations are intended to be included within the scope of the claims, where the term "comprising" means "including, but not limited to." Those familiar with the art may recognize other equivalents to the specific embodiments described herein which equivalents are also intended to be encompassed by the claims.

The invention claimed is:

1. An expandable medical device having a static state and at least one expanded state, the expandable medical device in said static state comprising:
    at least one first inner layer formed from a first polymer composition;
    at least one intermediate layer; and
    at least one second outer layer formed from a second polymer composition which is the same as or different than said first polymer composition, said at least one second outer layer having an inner surface and an outer surface and the at least one second outer layer comprising a closed lattice in said inner surface or said outer surface of said at least one second outer layer, the closed lattice is defined by channels having a thinner wall than corresponding areas of the outer surface; and
    wherein said lattice is closed in said static state and said at least one intermediate layer is unexposed and said lattice is open when said expandable medical device is in said at least one expanded state, exposing said intermediate layer.

2. The expandable medical device of claim 1 wherein said at least one intermediate layer comprises at least one lubricious polymer material, at least one therapeutic agent or a combination thereof.

3. The expandable medical device of claim 1 wherein said at least one intermediate layer comprises a lubricious gel.

4. The expandable medical device of claim 3 wherein said lubricious gel is a hydrogel.

5. The expandable medical device of claim 1 wherein said at least one intermediate layer comprises at least one therapeutic agent.

6. The expandable medical device of claim 1 wherein first polymer composition comprises a polyether-block-amide copolymer.

7. The expandable medical device of claim 1 wherein said closed lattice is in said outer surface of said at least one second outer layer.

8. The expandable medical device of claim 1 in combination with a catheter assembly, the catheter assembly having a distal end, the expandable medical device disposed on the distal end of said catheter assembly.

9. The expandable medical device of claim 1 in combination with a stent, said stent disposed on said expandable medical device.

10. The expandable medical device of claim 1, the device comprising cone, waist and body portions, the intermediate layer is on the body portion of the device.

11. An expandable medical device for the controlled, localized delivery of a therapeutic agent, said expandable medical device having at least one static state and at least one expanded state, said expandable medical device comprising:
    at least one first inner layer formed from a first polymer composition;
    at least one second outer layer formed from a second polymer composition which is the same as or different than said first polymer composition, said at least one second outer layer having an inner surface and an outer surface and the at least one second outer layer comprising a closed lattice in said inner surface or said outer surface of said at least one second outer layer, the closed lattice is defined by channels having a thinner wall than corresponding areas of the outer surface; and
    an intermediate layer, said intermediate layer comprising at least one therapeutic agent;
    wherein said lattice is closed in said static state and said intermediate layer is unexposed and said lattice is open when said expandable medical device is in said at least one expanded state, exposing said intermediate layer for delivery of said at least one therapeutic agent.

12. An expandable medical device for the delivery of an implantable medical device, said expandable medical device having a static state, at least one expanded state and at least one deflated state, said expandable medical device disposed at the distal end of a catheter assembly, said implantable medical device disposed about said expandable medical device when said expandable medical device is in said at least one deflated state, said expandable medical device comprising:
    at least one first inner layer formed from a first polymer composition;
    at least one second outer layer formed from a second polymer composition which is the same as or different than said first polymer composition, said at least one second outer layer having an inner surface and an outer surface and the at least one second outer layer comprising a closed lattice in said inner surface or said outer surface of said at least one second outer layer, the closed lattice is defined by channels having a thinner wall than corresponding areas of the outer surface; and an intermediate layer, said intermediate layer comprising at least one lubricious polymer material;

wherein in said static state said lattice is closed and said intermediate layer is unexposed and said lattice is open when said expandable medical device is in said at least one expanded state, exposing said intermediate layer.

13. An expandable medical device having a static state and at least one expanded state, the expandable medical device in said static state comprising:

at least one first inner layer formed from a first polymer composition; and at least one second outer layer formed from a second polymer composition which is the same as or different than said first polymer composition, said at least one second outer layer having an inner surface and an outer surface and the at least one second outer layer comprising a closed lattice in said inner surface or said outer surface of said at least one second outer layer, the closed lattice is defined by channels having a thinner wall than corresponding areas of the outer surface;

said lattice is open when said expandable medical device is in said at least one expanded state; and wherein fluid is prevented from flowing through the outer surface or inner surface of the at least one second outer layer when the lattice is closed and wherein fluid can flow through said outer surface of inner surface of said outer layer at least one second when said lattice is open.

* * * * *